US006847722B1

(12) United States Patent
Uosukainen et al.

(10) Patent No.: US 6,847,722 B1
(45) Date of Patent: Jan. 25, 2005

(54) METHOD AND EQUIPMENT FOR ATTENUATING SOUND IN A DUCT

(75) Inventors: Seppo Uosukainen, Helsinki (FI); Vesa Välimäki, Espoo (FI); Kari Kirjavainen, Espoo (FI); Jukka Lekkala, Tampere (FI); Hannu Nykänen, Tampere (FI)

(73) Assignee: VTT, Espoo (FI)

( * ) Notice: Subject to any disclaimer, the term of this patent is extended or adjusted under 35 U.S.C. 154(b) by 0 days.

(21) Appl. No.: 09/508,404

(22) PCT Filed: Sep. 9, 1998

(86) PCT No.: PCT/FI98/00705

§ 371 (c)(1), (2), (4) Date: Jun. 12, 2000

(87) PCT Pub. No.: WO99/14736

PCT Pub. Date: Mar. 25, 1999

(30) Foreign Application Priority Data

Sep. 12, 1997 (FI) ................................................ 973677

(51) Int. Cl.[7] ........................ A61F 11/06; G10K 11/06; H03B 29/00

(52) U.S. Cl. ..................................... 381/71.5; 381/71.7

(58) Field of Search ............................... 381/71.5, 71.1, 381/71.7

(56) References Cited

U.S. PATENT DOCUMENTS

| | | | | |
|---|---|---|---|---|
| 4,177,874 | A | 12/1979 | Angelini et al. | |
| 4,473,906 | A | 9/1984 | Warnaka et al. | |
| 5,060,271 | A | 10/1991 | Geddes | |
| 5,319,165 | A | 6/1994 | Geddes | |
| 5,548,653 | A | 8/1996 | Pla et al. | |
| 6,201,872 | B1 * | 3/2001 | Hersh et al. | 381/71.5 |

FOREIGN PATENT DOCUMENTS

| | | |
|---|---|---|
| FR | 2 438 796 | 5/1980 |
| GB | 2 160 742 | 12/1985 |

* cited by examiner

*Primary Examiner*—Xu Mei
*Assistant Examiner*—Con P. Tran
(74) *Attorney, Agent, or Firm*—Young & Thompson

(57) ABSTRACT

The invention relates to a method and an equipment for attenuating sound in a duct. Sound propagating in a duct is detected by means of a detector (2) and attenuated by using two successive monopole elements (3, 4) in such a way that both elements function as a dipole approximation and the elements are also used to approximatively produce the monopole radiation needed. A dipole control signal is fed to both elements (3, 4) at a phase shift which is 180° between the two elements. In addition, a monopole control signal is fed to the same elements (3, 4), only this time cophasally. Total volume velocities produced by the two elements (3, 4) are combinations of the portions obtained from the monopole and dipole sources.

11 Claims, 2 Drawing Sheets

METHOD AND EQUIPMENT FOR ATTENUATING SOUND IN A DUCT

BACKGROUND OF THE INVENTION

The invention relates to a method for attenuating sound in a duct, the sound to be attenuated being detected in the method by means of a detector and the attenuation being performed by means of two successive actuator elements.

The invention also relates to an equipment for attenuating sound in a duct, the equipment comprising a detector for detecting the sound to be attenuated and two successive actuator elements for producing a sound attenuating counter-sound.

One of the methods presented for attenuating sound in ducts is a method known as the Swinbanks method, in which an attenuation sound is produced by means of two successive elements. Both elements produce a volume velocity of an equal amplitude, the volume velocities being, however, of opposite phases. In addition, to the element that is first in the direction of propagation of the sound to be attenuated is caused a delay proportional to the distance between the elements. A unidirectional, radiating element is thereby obtained, i.e. no acoustic feedback is caused to the detector measuring the sound to be attenuated. Instead, a signal is generated that only attenuates forward the sound of the sound source to be attenuated. To digitally implement inter-channel delay in different elements occupies, however, a great amount of signal processing resources, which means that the equipment to be used must have an extensive capacity and/or the processing time becomes inconveniently long.

SUMMARY OF THE INVENTION

An object of the present invention is to provide a method and an equipment that will allow the advantages of the above mentioned method to be obtained, avoiding, however, the above disadvantages.

A method of the invention is characterized in that sound is attenuated by means of two successive monopole elements in such a way that both elements function as a dipole approximation and also produce a monopole radiation needed, a dipole control signal being fed to both elements at a phase shift which is 180° between the two elements and a monopole control signal being fed to the elements cophasally.

Further, an equipment of the invention is characterized in that the actuator elements are monopole elements which are arranged to function as a dipole approximation and to also produce the monopole radiation needed and that the equipment comprises means for feeding the dipole control signal to both elements at a phase shift which is 180° between the two elements and for feeding a monopole control signal to the elements cophasally.

An essential idea of the invention is that sound is attenuated by means of two successive monopole elements in such a way that both elements function as a dipole approximation and that, in an equal manner, they are also used for approximately producing the monopole radiation needed. The dipole control signal is fed to both elements at a phase shift which is 180° between the two elements. (The monopole control signal is also fed to the same elements, only this time cophasally. Total volume velocities produced by both elements are combinations of the portions obtained from the monopole and dipole sources. An idea of a preferred embodiment is that control signals are specified by means of suitable control functions.

An advantage of the invention is that the equipment does not produce acoustic feedback between an actuator and the detector, because the equipment provides a unidirectional signal. In addition, the equipment is simple and in the control system of the equipment there is no inter-channel delay in the different elements, so when the equipment is used it is possible to apply simple algorithms and short processing times, while maintaining at the same time a good performance level. The use of control functions for specifying and correcting control signals allows an almost ideal system functionality to be obtained also at higher frequencies.

The term 'duct' is used in the present application to refer to a duct or a conduit, or the like, in which sound propagates substantially in only two directions at frequencies low enough.

BRIEF DESCRIPTION OF THE DRAWINGS

The invention will be described in greater detail in the attached drawings, in which.

DESCRIPTION OF THE PREFERRED EMBODIMENTS

Figure 1:
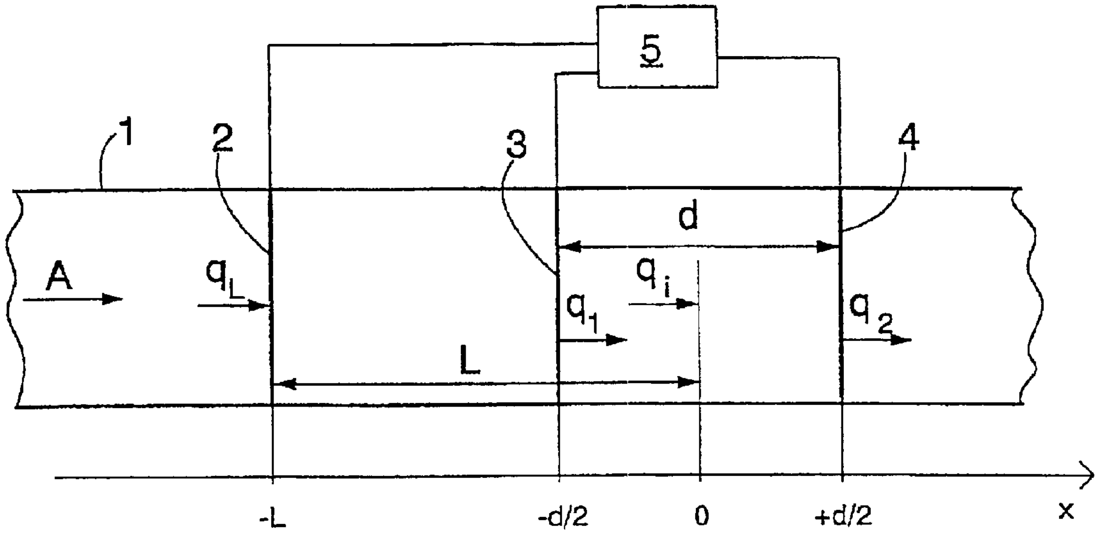
FIG. 1 is a schematic side view, in section, of an equipment of the invention.

FIG. 1 shows a duct 1. Sound appearing in the duct 1, caused by a sound source, is depicted with an arrow A. At a point $x=-L$ is arranged a detector 2 which is used for detecting the sound caused by the sound source. In the direction of sound propagation, a first actuator element 3 is placed after the detector 2 at a point $x=-d/2$ and a second actuator element 4 is placed after the first one at a point $x=+d/2$, the actuator elements 3 and 4 being at a distance d from each other. The actuator elements 3 and 4 are monopole elements, therefore they do not impede the flow of a medium in the duct 1. FIG. 1 also schematically shows control means 5 for controlling actuator elements 3 and 4 on the basis of a signal received from the detector 2.

The first actuator element 3 produces a volume velocity $q_1$ and the second actuator element 4 produces a volume velocity $q_2$. Both actuator elements 3 and 4 function as a dipole approximation in such a way that a dipole control signal is fed to both elements 3 and 4 at a phase shift which is 180° between the two elements. In addition, a monopole control signal is fed to both elements 3 and 4, only this time cophasally. The total volume velocities $q_1$ and $q_2$ produced by the elements 3 and 4 are combinations of the portions obtained from monopole and dipole sources.

The volume velocity $q_1$ describes the sound produced by the sound source at a point x=0, the volume velocity $q_i$ being proportional to the original sound pressure $P_1$ such that $$q_1 = \frac{p_1 S}{\rho_0 c_0},$$

where S is the cross-sectional area of the duct, $p_0$ is the density of the medium in a static state and $c_0$ is the sound velocity in the medium.

The control signals of the actuator elements 3 and 4, i.e. the total volume velocities they produce, are $$q_1=\tfrac{1}{2}(1/jkd-\tfrac{1}{2})q_i,\ x=-d/2$$

and $$q_2=-\tfrac{1}{2}(1/jkd+\tfrac{1}{2})q_i,\ x=+d/2,$$

where j is an imaginary unit;

k is a wave number=$\omega/c_0$;

$\omega$ is an angular frequency;

$c_0$ is sound velocity in a medium; and $q_i$ is the original sound pressure to be attenuated, located at the point x=0 and converted to a volume velocity quantity.

In the volume velocity expressions, the first parts relate to dipole radiation and the latter parts to monopole radiation.

The above described total volume velocities attenuate the sound produced by a sound source in the direction of propagation of the sound, and the actuator elements 3 and 4 do not radiate against the direction of sound of the sound source. At higher frequencies, however, the system does not function ideally, due to the approximative nature of the monopole and dipole radiation. Errors produced by the approximations can be compensated by means of suitable control functions. A dipole control function denoted by a quantity a and a monopole control function denoted by a quantity b allow the following total volume velocities to be obtained:

$$q_1=\tfrac{1}{2}(a/jkd-b/2)q_i,\ x=-d/2,$$

and $$q_2=-\tfrac{1}{2}(a/jkd+b/2)q_i,\ x=+d/2.$$

Figure 2:
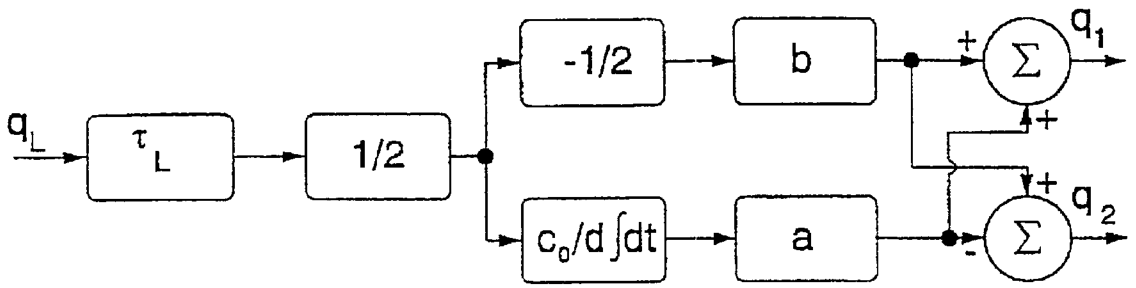
FIG. 2 is a diagram illustrating a control system of the invention.

The control system of the actuator elements 3 and 4 is shown as a diagram in FIG. 2. In FIG. 2 a quantity $q_i$ denotes a signal measured by the detector 2, the signal being converted to a volume velocity quantity, and a delay $\tau_L$ denotes the time required for sound to propagate from the detector point x=−L to the actuator system centre x=0, i.e. $\tau_L=L/c_0$, where $c_0$ denotes sound velocity in the medium. The delay in question can be estimated and implemented by means of an adaptive filter. In the embodiment shown in FIG. 2 the imaginary unit j is replaced with an integrator, which allows the previously needed 90° phase shift and also the singularity of the control function at the frequency 0 to be avoided.

Errors produced by the approximations can be corrected for instance by applying the following dipole part control function $$a=\frac{kd/2}{\sin(kd/2)}$$

and the following monopole part control function $$b=\frac{1}{\cos(kd/2)}$$

Figure 3:
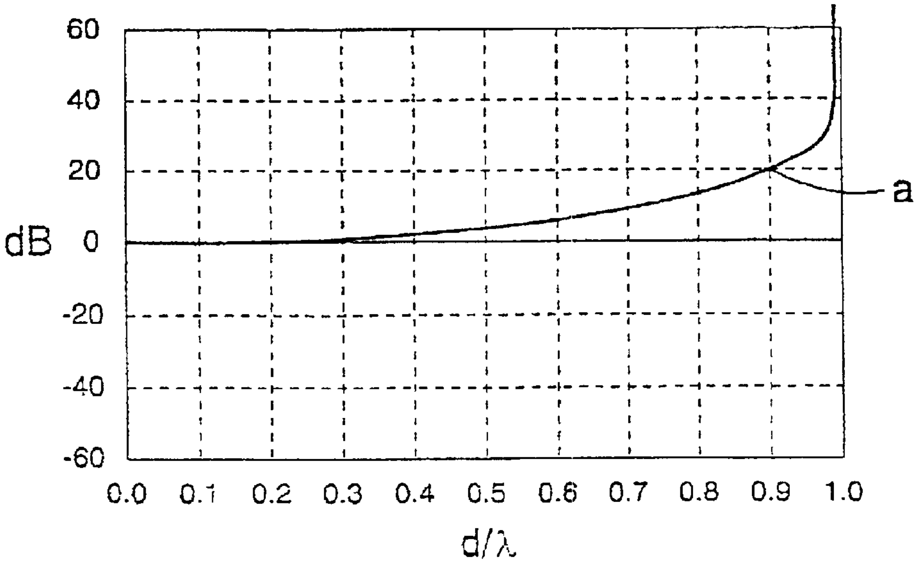
FIG. 3 illustrates a control function of a dipole part.
Figure 4:
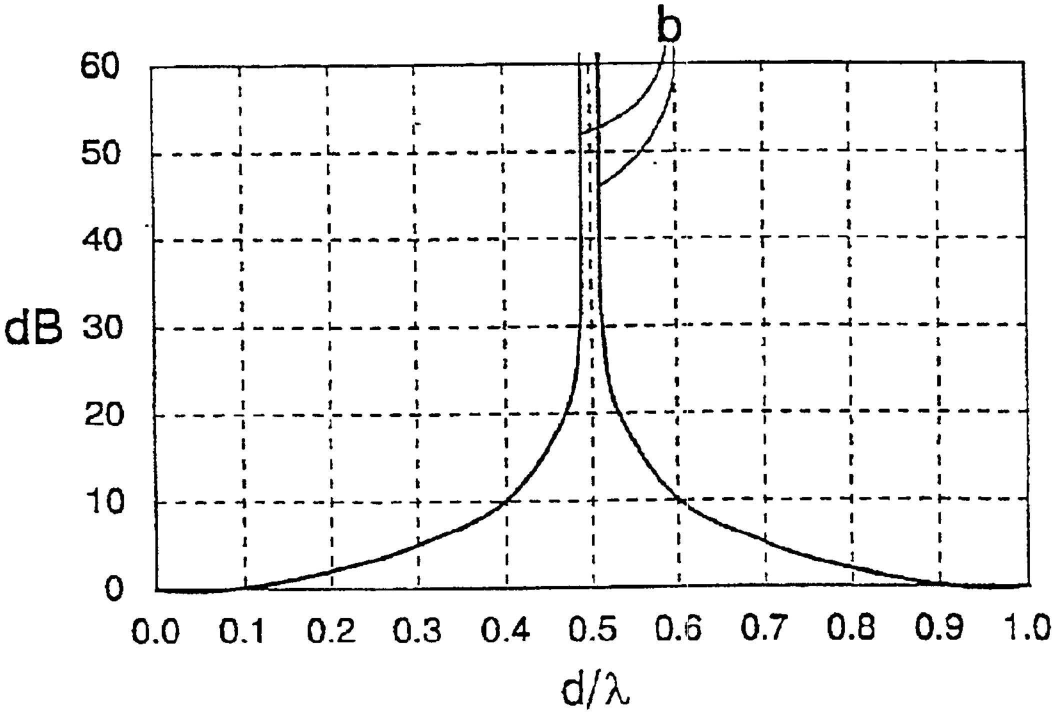
FIG. 4 illustrates a control function of a monopole part.

A graph illustrating the dipole part control function a is shown in FIG. 3 and a graph illustrating the monopole part control function b is shown in FIG. 4. A quantity $\lambda$ in FIGS. 3 and 4 denotes wave length. Monopole control is singular when d=$\lambda$/2. The continuous frequency area available is thus restricted to a frequency corresponding to the wave length in question.

The drawings and the related description are only meant to illustrate the inventive idea. The details of the invention may vary within the scope of the claims. An arrangement of the invention can thus also be used in a detector implementation. The most ideal function of an arrangement of the invention is obtained when the frequency is sufficiently low, ensuring that sound propagates only in a plane wave form only in the duct. The duct is most advantageously sufficiently long, so as to ensure that reflections from the duct ends do not affect the final result. In addition, the walls of the duct are most advantageously so hard that duct wall impedance need not to be taken into account. Further, the medium in the duct is most advantageously homogenous and motionless, sound velocity being equally high at every point of the duct and not dependent on the direction of sound propagation. Further, the medium is most advantageously so ideal that viscosity or thermal loss do not affect the final result.

What is claimed is:

1. A method for attenuating sound in a duct, the sound to be attenuated being detected in the method by means of a detector (2) and the attenuation being performed by means of two successive actuator elements (3, 4), wherein sound is attenuated by means of two successive monopole elements (3, 4) in such a way that both elements (3, 4) function as a dipole approximation and also produce a monopole radiation needed, a dipole control signal being fed to both elements (3, 4) at a phase shift which is 180° between the two elements and a monopole control signal being fed to the elements (3, 4) cophasally, wherein the control signal of the first actuator element (3) is $$q_1=\tfrac{1}{2}(a/jkd-b/2)q_i,$$

and the control signal of the second actuator element (4) is $$q_2=-\tfrac{1}{2}(a/jkd+b/2)q_i,$$

where j is an imaginary unit;

k is a wave number=$\omega/c_0$;

$\omega$ is an angular frequency;

$c_0$ is sound velocity in a medium;

d is a distance between the actuator elements (3, 4);

$q_i$ is the sound pressure to be attenuated, located at the center of the actuator elements (3, 4), and converted to a volume velocity quantity;

a is a constant or a dipole part control function; and b is a constant or a monopole part control function.

2. A method for attenuating sound in a duct, comprising the steps of:

detecting sound in a duct that is to be attenuated;

generating dipole control signals based on the detected sound for two successive actuator elements in the duct that produce a unidirectional signal in plane wave form, the generated dipole control signals having a phase shift of 180° with each other;

generating monopole control signals based on the detected sound for the two elements, the generated monopole control signals being in phase with each other; and combining the respective dipole and monopole control signals for each of the two elements and feeding the combined signals to the two elements, respectively, to produce the unidirectional signal in plane wave form, wherein the combined control signal for a first of the successive actuator elements is $$q_1=\tfrac{1}{2}(a/jkd-b/2)q_i,$$

and the combined control signal for a second of the successive actuator elements is $$q_2=\tfrac{1}{2}(a/jkd+b/2)q_i,$$

where j is an imaginary unit;

k is a wave number=$\omega/c_0$;

$\omega$ is an angular frequency;

$c_0$ is sound velocity in a medium;

d is a distance between the actuator elements;

$q_i$ is the sound pressure to be attenuated, located at the center of the actuator elements (3, 4), and converted to a volume velocity quantity;

a is a constant or a dipole part control function; and b is a constant or a monopole part control function.

3. The method according to claim 2, wherein "a" is a dipole part control function and "b" is a monopole part function such that $$a=\frac{kd/2}{\sin(kd/2)}$$

and $$b=\frac{1}{\cos(kd/2)}.$$

4. The method according to claim 2, wherein, in the control signals ($q_1$, $q_2$) of the elements, the impact of the imaginary unit is determined by using an integrator.

5. An equipment for attenuating sound in a duct, the equipment comprising:

a detector (2) for detecting the sound to be attenuated; and two successive actuator elements (3, 4) for producing a sound attenuating counter-sound, wherein the actuator elements (3, 4) are monopole elements which are arranged to function as a dipole approximation and to also produce a necessary monopole radiation and that the equipment comprises means for feeding a dipole control signal to both elements (3, 4) at a phase shift which is 180° between the two elements and for feeding a monopole control signal to the elements (3, 4) cophasally, wherein the control signal of the first actuator element (3) is $$q_1=\tfrac{1}{2}(a/jkd-b/2)q_i,$$

and the control signal of the second actuator element (4) is $$q_2=-\tfrac{1}{2}(a/jkd+b/2)q_i,$$

where j is an imaginary unit;

k is a wave number=$\omega/c_0$;

$\omega$ is an angular frequency;

$c_0$ is sound velocity in a medium;

d is a distance between the actuator elements (3, 4);

$q_1$ is the sound pressure to be attenuated, located at the center of the actuator elements (3, 4), and converted to a volume velocity quantity;

a is a constant or a dipole part control function; and b is a constant or a monopole part control function.

6. An equipment for attenuating sound in a duct, comprising:

a detector that detects sound in a duct that is to be attenuated;

two successive actuator elements in the duct that produce a unidirectional signal in plane wave form; and a control unit that generates dipole control signals based on the detected sound for said two elements, the generated dipole control signals having a phase shift of 180° with each other, that generates monopole control signals based on the detected sound for said two elements, the generated monopole control signals being in phase with each other, and that combines the respective dipole and monopole control signals for each of said two elements and feeds the combined signals to said two elements, respectively, to produce the unidirectional signal in plane wave form, wherein the combined control signal for a first one of the actuator elements is $$q_1=\tfrac{1}{2}(a/jkd-b/2)q_i,$$

and the combined control signal for a second one of the actuator elements is $$q_2=\tfrac{1}{2}(a/jkd+b/2)q_i,$$

where j is an imaginary unit;

k is a wave number=$\omega/c_0$;

$\omega$ is an angular frequency;

$c_0$ is sound velocity in a medium;

d is a distance between the actuator elements;

$q_1$ is the sound pressure to be attenuated, located at the centre of the actuator elements (3, 4), and converted to a volume velocity quantity;

a is a constant or a dipole part control function; and b is a constant or a monopole part control function.

7. The equipment according to claim 6, wherein "a" is a dipole part control function and "b" is a monopole part function such that $$a=\frac{kd/2}{\sin(kd/2)}$$

and $$b=\frac{1}{\cos(kd/2)}.$$

8. The method according to claim 3, wherein, in that the control signals ($q_1$, $q_2$) of the elements, the impact of the imaginary unit is determined by using an integrator.

9. The method according to claim 1, wherein "a" is a dipole part control function and "b" is a monopole part function such that $$a = \frac{kd/2}{\sin(kd/2)}$$

and $$b = \frac{1}{\cos(kd/2)}.$$

10. The method according to claim 1, wherein, in the control signals ($q_1$, $q_2$) of the elements, the impact of the imaginary unit is determined by using an integrator.

11. The equipment according to claim 5, wherein "a" is a dipole part control function and "b" is a monopole part function such that $$a = \frac{kd/2}{\sin(kd/2)}$$

and $$b = \frac{1}{\cos(kd/2)}.$$

* * * * *